US00PP18382P3

(12) United States Plant Patent
Konst

(10) Patent No.: US PP18,382 P3
(45) Date of Patent: Jan. 1, 2008

(54) ***ALSTROEMERIA* PLANT NAMED 'KONPULSE'**

(50) Latin Name: *Alstroemeria*
Varietal Denomination: Konpulse

(75) Inventor: Johannes Wilhelmus Maria Konst, GA Nieuwveen (NL)

(73) Assignee: Konst Breeding B.V., Nieuwveen (NL)

( * ) Notice: Subject to any disclaimer, the term of this patent is extended or adjusted under 35 U.S.C. 154(b) by 0 days.

(21) Appl. No.: 11/438,818

(22) Filed: May 23, 2006

(65) Prior Publication Data

US 2007/0277272 P1 Nov. 29, 2007

(51) Int. Cl.
*A01H 5/00* (2006.01)

(52) U.S. Cl. ..... Plt./309

(58) Field of Classification Search ..... Plt./309
See application file for complete search history.

*Primary Examiner*—Kent Bell
*Assistant Examiner*—Annette H Para
(74) *Attorney, Agent, or Firm*—Jondle & Associates, P.C.

(57) ABSTRACT

A new *alstroemeria* plant particularly distinguished by cup-shaped, orange-red to red flowers with yellow spots and green nerves, compact, vigorous, free branching growth habit and a continuous flowering response from late spring to fall is disclosed.

2 Drawing Sheets

Genus and species: *Alstroemeria.*
Variety denomination: 'Konpulse'.

BACKGROUND OF THE NEW PLANT

The present invention comprises a new and distinct cultivar of *alstroemeria,* botanically known as *Alstroemeria* and hereinafter referred to by the cultivar name 'Konpulse'. The new cultivar originated from a hybridization made in November 1999 in Nieuwveen, The Netherlands. The female parent was the proprietary *alstroemeria* plant '3150-30' (unpatented), while the male parent was the proprietary *alstroemeria* plant '5261-4' (unpatented).

The new cultivar was created in 1999 in Nieuwveen, The Netherlands and has been asexually reproduced repeatedly by in vitro rhizome division in Nieuwveen, The Netherlands over a three year period. The present invention has been found to retain its distinctive characteristics through successive asexual propagations.

Plants Breeder's Rights for this cultivar were applied for with the European Union on Apr. 10, 2006.

SUMMARY OF THE INVENTION

The following are the most outstanding and distinguishing characteristics of this new cultivar when grown under normal horticultural practices in Nieuwveen, The Netherlands.

1) Cup-shaped, orange-red to red flowers with yellow spots and green nerves; and
2) Compact, vigorous and free branching growth habit; and
3) Continuous flowering response from late spring to fall.

DESCRIPTION OF PHOTOGRAPHS

This new *alstroemeria* plant is illustrated by the accompanying photographs which show the overall plant habit including blooms, buds and foliage of the plant; the colors shown are as true as can be reasonably obtained by conventional photographic procedures. The photographs are of a 24-week old plant grown in a greenhouse for the first 18-weeks and then transferred outside in the Spring-Summer in Nieuwveen, The Netherlands.

DESCRIPTION OF THE NEW CULTIVAR

Figure 1:
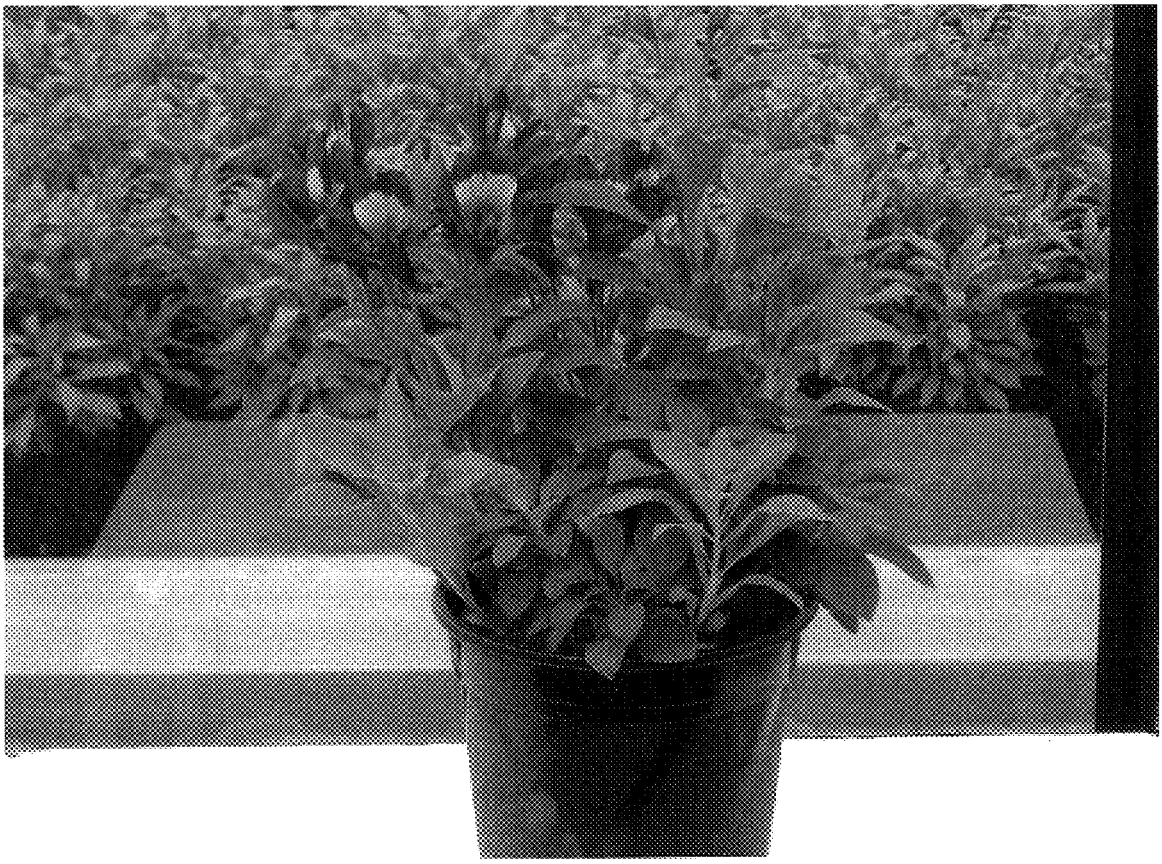
FIG. 1 shows the overall plant habit, including blooms, buds and foliage.
Figure 2:
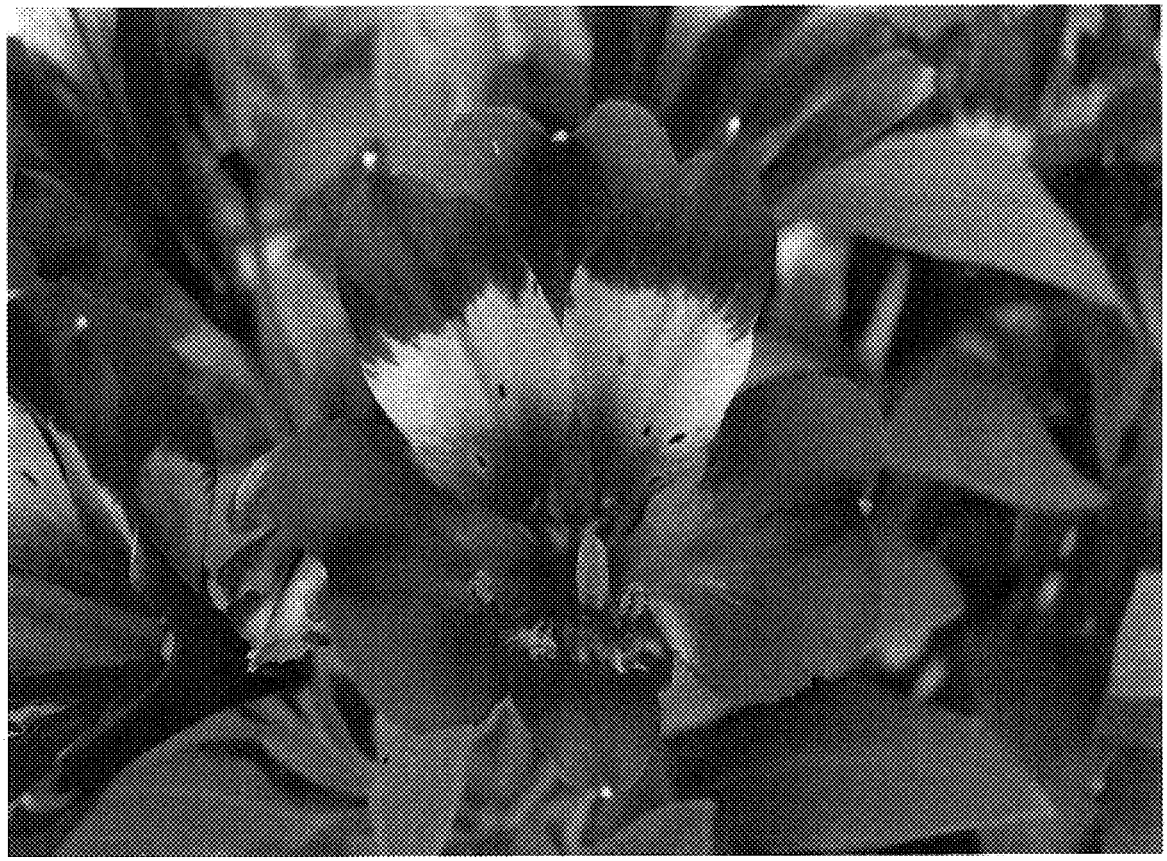
FIG. 2 shows the mature flower.

The following detailed description sets forth the distinctive characteristics of 'Konpulse'. The data which define these characteristics were collected from asexual reproductions carried out in Nieuwveen, The Netherlands. The plant history was taken on 36-week old plants which were planted as rooted cuttings in 19-cm to 33-cm pots in 2005 and grown in a glass greenhouse between 6° C. and 30° C. for the first 18 weeks and then transferred outside the greenhouse. Observations were made when the plants were in full in September 2005. Color readings were taken under natural light in the greenhouse. Color references are primarily to the R.H.S. Colour Chart of The Royal Horticultural Society of London (R.H.S.) (2001).

DETAILED BOTANICAL DESCRIPTION

Classification:
*Family.*—Liliaceae.
*Botanical.*—*Alstroemeria.*
*Common name.*—*Alstroemeria*, Peruvian lily, Lily of the Incas.

Parentage:
*Female parent.*—'3150-30', a proprietary red-flowered *alstroemeria* plant (unpatented).
*Male parent.*—'5261-4', a proprietary red-flowered *alstroemeria* plant (unpatented).

Growth:
*Form.*—Perennial.
*Habit.*—Compact, freely branching, vigorous.

*Overall plant shape.*—Bowl-shaped.
*Height.*—30.0 cm.
*Diameter or area of spread.*—48 cm.
*Propagation.*—In vitro rhizome division.
*Time to produce a flowering plant.*—6 to 14 weeks after stem initiation.
*Time to produce a finished flowering plant.*—18 weeks for a 19-cm to 33-cm pot.
*Keeping quality.*—14 days.
*Outdoor plant performance.*—Medium tolerance to high temperatures; not frost resistant; use as garden plants.
*Rhizome.*—Shape: Elongate, rounded with basal branching. Color: RHS 162D. Length: 4.0 cm. Diameter: 0.7 cm. Texture: Smooth.

Stems:
*Shape.*—Round.
*Aspect.*—Upright.
*Strength.*—Sturdy.
*Color.*—RHS 144A.
*Diameter of stems and lateral branches.*—0.5 cm.
*Length of stems and lateral branches.*—30 cm.
*Number of lateral branches.*—Numerous.
*Internode length.*—0.7 cm to 1.9 cm.
*Pubescence.*—Absent.

Leaves:
*Arrangement.*—Scattered; leaves are turned upside down.
*Durability to stresses.*—Medium.
*Quantity of leaves per lateral branch.*—16.
*Shape.*—Obovate.
*Apex.*—Pointed.
*Base.*—Narrow.
*Margin.*—Entire.
*Color (mature leaves).*—Upper surface: RHS 137D. Lower surface: RHS 137C.
*Color (immature leaves).*—RHS 144A (both surfaces).
*Size.*—Length: Upper part: 12.0 cm. Lower part: 4.8 cm. Width: Upper part: 3.9 cm. Lower part: 1.3 cm.
*Texture.*—Glabrous.
*Venation.*—Type: Parallel. Color: Upper surface: RHS 138B. Lower surface: RHS 144A.
*Pubescence.*—Absent.

Flower buds:
*Color.*—RHS 53A with RHS 143A (green) nerves.
*Shape.*—Oval.
*Size.*—Length: 3.5 cm. Diameter: 1.6 cm.

Inflorescence:
*Blooming habit.*—Free and continuous from late Spring to Fall; self-cleaning.
*Inflorescence type and arrangement.*—Single cup-shaped flowers arranged in a compound umbel.
*Height.*—10.4 cm.
*Width.*—10.5 cm.
*Fragrance.*—None.
*Quantity of flowers per inflorescence.*—2 to 10.
*Quantity of flowers per lateral stem.*—1.
*Quantity of flowers buds per lateral stem.*—1 to 3.
*Quantity of flowers and buds per plant.*—25 to 100.
*Flower longevity on the plant.*—7 to 20 days (depending on temperature).
*Flower longevity as a cut flower.*—7 to 14 days (depending on temperature).
*Peduncle.*—Color: RHS 143C with spots of RHS 187A. Length: 1.5 cm. Diameter: 0.2 cm. Angle: 20°. Strength: Strong. Texture: Smooth.
*Pedicel.*—Color: RHS 187A with RHS 143C spots. Length: 2.5 cm. Diameter: 0.2 cm. Angle: 15°. Strength: Strong.

Flowers:
*Type/form.*—Cup-shaped.
*Size.*—Height (flower depth): 6.2 cm. Diameter: 4.3 cm.
*Aspect.*—Outward.

Perianth:
*Arrangement.*—Six segments arranged in two whorls, each whorl composed of two lateral and one median segment.
*Inner tepals.*—Number of tepals: 3, two lateral and one median. Appearance: Dull. Texture (both surface): Smooth. Shape: Lanceolate. Apex: Pointed. Base: Attenuate. Margin: Entire. Length: Lateral segments: 5.6 cm. Median segment: 4.9 cm. Width: Lateral segments: 1.2 cm. Median segment: 1.2 cm. Color (when opening): Lateral segments: Upper surface: RHS 151D with RHS 53B tip. Lower surface: RHS 53B with RHS 1B spots. Median segment: Upper surface: RHS 45A with RHS 1B spots. Lower surface: RHS 53C with RHS 1B spots. Color (fully opened): Lateral segments: Upper surface: RHS 39B base, RHS 14A center and RHS 46B tip. Lower surface: RHS 46B. Median segment: Upper surface: RHS 46B. Lower surface: RHS 42B base, RHS 144A spots and RHS 53C tip. Colors fading to: RHS 34A base and RHS 53B tip for all segments; markings do not fade.
*Outer tepals.*—Number of tepals: 3, two lateral and one median. Appearance: Dull. Texture (both surfaces): Smooth. Shape: Round. Apex: Obovate with a long and small lower part. Base: Attenuate. Margin: Entire. Length: Lateral segments: 4.7 cm. Median segment: 4.7 cm. Width: Lateral segments: 1.9 cm. Median segment: 1.8 cm. Color (when opening): Lateral segements: Upper surface: RHS 53B. Lower surface: RHS 53B with RHS 143C nerve. Median segment: Upper surface: RHS 53B. Lower surface: RHS 46A. Color (fully opened): Lateral segements: Upper surface: RHS 45A. Lower surface: RHS 53B. Median segment: Upper surface: RHS 53B. Lower surface: RHS 46A. Colors fading to: RHS 53B for all segments; markings do not fade.

Reproductive organs:
*Stamens.*—Quantity: 6. Anther: Shape: Oval. Size: Length: 0.7 cm. Width: 0.2 cm. Color: RHS 162A. Pollen: Abundant. Pollen color: RHS 198A.
*Pistil.*—Quantity: One. Length: 4.1 cm.
*Style.*—Length: 3.5 cm. Color: RHS 53C.
*Stigma.*—Shape: Pistil divided into 3 curled parts. Color: RHS 53A.
*Ovary color.*—Upper surface: RHS 59A. Lower surface: RHS 146B.

Fruit and seed set:
*Seed.*—Quantity: 1 to 5. Shape: Round with extended nerves. Length: 0.3 cm. Diameter: 0.3 cm. Color: RHS 164A.
*Fruit.*—Number of fruit per flower: 1. Length: 0.7 cm. Diameter: 0.7 cm. Color: RHS 141C with some RHS 166A.

Disease and insect resistance: No particular resistance or susceptibility to diseases or insects noted to date.

COMPARISON WITH COMMERCIAL CULTIVAR

A comparison with the female parent, a proprietary *alstroemeria* plant, '3150-30' (unpatented), is not possible because detailed information is unknown.

A comparison with the male parent, a proprietary *alstroemeria* plant, '5261-4' (unpatented), is not possible because detailed information is unknown.

'Konpulse' is similar to the commercial variety 'California' (unpatented) however, there are differences as listed in Table 1 below:

TABLE 1

Comparison of Characteristics between 'Konpulse' and 'California'

| Characteristic | 'Konpulse' | 'California' |
|---|---|---|
| Overall plant shape | Bowl-shaped | Bushy |
| Quantity of leaves per lateral branch | 16 | 36 |
| Leaf shape | Obovate | Lanceolate |
| Inflorescence height | 10.4 cm | 18.3 cm |
| Inflorescence width | 10.5 cm | 19.5 cm |
| Quantity of flowers per inflorescence | 2 to 10 | 3 to 18 |
| Inner tepal colors, fading to: | RHS 34A (orange-red) base and RHS 53B (red) tip | RHS 11B (yellow) |
| Outer tepal colors, fading to: | RHS 53B (red) | RHS 11B (yellow) |
| Pedicel length | 2.5 cm | 1.4 cm |

I claim:

1. A new and distinct cultivar of *alstroemeria* plant as shown and described herein.

* * * * *